(12) United States Patent
Olschewski

(10) Patent No.: US 7,280,203 B2
(45) Date of Patent: Oct. 9, 2007

(54) METHOD FOR SETTING A FLUORESCENCE SPECTRUM MEASUREMENT SYSTEM FOR MICROSCOPY

(75) Inventor: Frank Olschewski, Heidelberg (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 305 days.

(21) Appl. No.: 10/924,658

(22) Filed: Aug. 24, 2004

(65) Prior Publication Data

US 2005/0046835 A1 Mar. 3, 2005

(30) Foreign Application Priority Data

Aug. 27, 2003 (DE) .............................. 103 39 312

(51) Int. Cl.
*G01J 3/30* (2006.01)
*F21V 9/16* (2006.01)

(52) U.S. Cl. .................................. 356/317; 250/459.1

(58) Field of Classification Search ..................... None
See application file for complete search history.

(56) References Cited

U.S. PATENT DOCUMENTS

| 3,013,467 | A  | * | 12/1961 | Minsky ...................... 356/432 |
| 6,483,103 | B2 | * | 11/2002 | Engelhardt et al. ......... 250/226 |
| 6,576,476 | B1 | * | 6/2003  | Taylor et al. ................ 436/172 |
| 6,618,140 | B2 | * | 9/2003  | Frost et al. .................. 356/317 |
| 6,947,127 | B2 | * | 9/2005  | Wolleschensky et al. ...... 356/73 |
| 6,947,133 | B2 | * | 9/2005  | Wolleschensky et al. ... 356/317 |
| 6,958,811 | B2 | * | 10/2005 | Wolleschensky et al. ... 356/326 |
| 7,130,043 | B2 | * | 10/2006 | Natori ........................ 356/318 |
| 2003/0139886 | A1 | * | 7/2003 | Bodzin et al. ................ 702/28 |
| 2003/0151741 | A1 | * | 8/2003 | Wolleschensky et al. ... 356/317 |
| 2003/0231825 | A1 | * | 12/2003 | Olschewski ................... 385/27 |
| 2005/0024637 | A1 | * | 2/2005 | Olschewski .................. 356/318 |
| 2005/0046835 | A1 | * | 3/2005 | Olschewski .................. 356/317 |
| 2005/0046836 | A1 | * | 3/2005 | Olschewski .................. 356/318 |
| 2005/0109949 | A1 | * | 5/2005 | Olschewski .............. 250/458.1 |
| 2005/0179892 | A1 | * | 8/2005 | Gerstner et al. ............ 356/318 |

FOREIGN PATENT DOCUMENTS

DE 100 06 800 8/2001
DE 102 27 111 12/2003

OTHER PUBLICATIONS

Bernhard Zimmerman, Going New Ways in Confocal Multifluorescence Imaging, Imaging Microscopy, Apr. 2002.*
Denis Demandolx et al., Guidelines for Multifluorescence Confocal Imaging: Acquisition, Processing and Display, http://persp.magic.fr/demandolx/these/ma/ma.html.*
Carl Zeiss Advanced Imaging Microscopy, Spectral Separation of Multifluorescence Labels with the LSM 510 META.*
Demandolx, D., et al., "Multicolor analysis and local image correlation in confocal microscopy", Journal of Microscopy, vol. 185, Pt. 1, Jan. 1997, pp. 21-36.

* cited by examiner

*Primary Examiner*—Gregory J. Toatley, Jr.
*Assistant Examiner*—Jonathan Skovholt
(74) *Attorney, Agent, or Firm*—Houston Eliseeva LLP

(57) ABSTRACT

A method for separating fluorescence spectra of dyes present in a specimen (15) is disclosed. Firstly a spectral scan of the fluorescence spectrum of all the dyes present in the specimen (15) is performed. The fluorescence spectra associated with the respective dyes are stored in a database of the computer system. After spectral deconvolution of the acquired mixed fluorescence spectrum, a comparison is made between the measured individual spectra ascertained by spectral deconvolution and the fluorescence spectra associated with the respective dyes. Lastly, a linear deconvolution of the acquired mixed fluorescence spectrum is performed.

6 Claims, 3 Drawing Sheets

METHOD FOR SETTING A FLUORESCENCE SPECTRUM MEASUREMENT SYSTEM FOR MICROSCOPY

RELATED APPLICATIONS

This application claims priority of the German patent application 103 39 312.9 which is incorporated by reference herein.

FIELD OF THE INVENTION

The invention concerns a method for separating fluorescence spectra of dyes present in a sample.

BACKGROUND OF THE INVENTION

German Patent Application DE 100 06 800.6 discloses an apparatus for selection and detection of at least one spectral region of a spectrally spread light beam (spectral photometer, hereinafter a SP module). Selection means that are embodied as sliders are provided in the spread-out beam of the light coming from the specimen to be examined, in order thereby to direct portions of the spread-out light beam to various detectors. The signals of the detectors are then used for image generation. DE 100 06 800.6 does not disclose actuation of the sliders so as to enable rapid and reliable detection of a specific spectrum.

German Patent Application DE 102 27 111.9 discloses a spectral microscope and a method for data acquisition using a spectral microscope. Methods and systems for sensing maximum information from a fluorescing microscopic specimen are encompassed. Error-tolerant and adapting data acquisition is not, however, possible with this method.

In the multicolor analysis described by Demandolx and Davoust, biological structures are localized by the introduction of individual dyes (see Demandolx, Davoust: Multicolor Analysis and Local Image Correlation in Confocal Microscopy, Journal of Microscopy, Vol. 185, Pt. 1, January 1997, pp. 21-36). If a structure reacts to one dye, this is referred to as "localization." If a structure reacts simultaneously to more than one dye, this is referred to as "co-localization," and the number of straight lines observable in the intensity vector space is greater than the number of dyes. This state of affairs is made visible by way of a sophisticated visualization method in the context of analysis. The "cytofluorogram" technique introduced by Demandolx and Davoust visualizes an ensemble of two-dimensional intensities $\{\overline{I}_i\}$ (in microscopy, the pixels of an image, voxels of a volume, or a chronologically successive series thereof; in cytofluorometry, the measurements of several samples) as a two-dimensional scatter plot that substantially represents a two-dimensional frequency distribution. On this basis, an estimate is obtained of the combined probability function of the intensities $\overline{I}$, a method which is existing art in mathematical data analysis and whose quality depends only on the size of the ensemble. With suitable color coding and graphical depiction, an image of the intensity distribution is obtained in which the straight lines are localized by the user's eye as widened tracks. The widening exists as a result of all forms of noise, as well as chemical influences possibly acting in the background.

SUMMARY OF THE INVENTION

It is the object of the invention to create a method for separating fluorescence spectra of dyes present in a sample that is error-tolerant and permits adaptation to spectral changes.

The aforesaid object is achieved by way of a method for separating fluorescence spectra of dyes present in a specimen, comprising the steps of:

acquiring a spectral scan and thereby ascertaining a mixed fluorescence spectrum of all the dyes present in the specimen;

communicating by way of a user, to a computer system associated with a scanning microscope, the dyes present in the specimen, the fluorescence spectra associated with the respective dyes being stored in a database of the computer system;

spectrally deconvoluting the acquired mixed fluorescence spectrum;

comparing the measured individual spectra ascertained by spectral deconvolution with the fluorescence spectra associated with the respective dyes; and linearly deconvoluting the acquired mixed fluorescence spectrum.

As compared with the existing art, the method has the advantage that a safeguard function protects the user from errors. For example, firstly a spectral scan is acquired, and a mixed fluorescence spectrum of all the dyes present in the specimen is thereby ascertained. The dyes present in the specimen are communicated by a user to a computer system associated with a scanning microscope, the fluorescence spectra associated with the respective dyes being stored in a database of the computer system. A spectral deconvolution of the acquired mixed fluorescence spectrum is performed, and then the measured individual spectra are compared with the fluorescence spectra associated with the respective dyes. Lastly, a linear deconvolution of the acquired mixed fluorescence spectrum is performed.

In addition, a warning is issued to the user if the comparison between the measured individual spectra ascertained by spectral deconvolution and the fluorescence spectra associated with the respective dyes yields an absence of agreement.

BRIEF DESCRIPTION OF THE DRAWINGS

The subject matter of the invention is depicted schematically in the drawings and will be described below with reference to the Figures, in which.

DETAILED DESCRIPTION OF THE INVENTION

Figure 1:
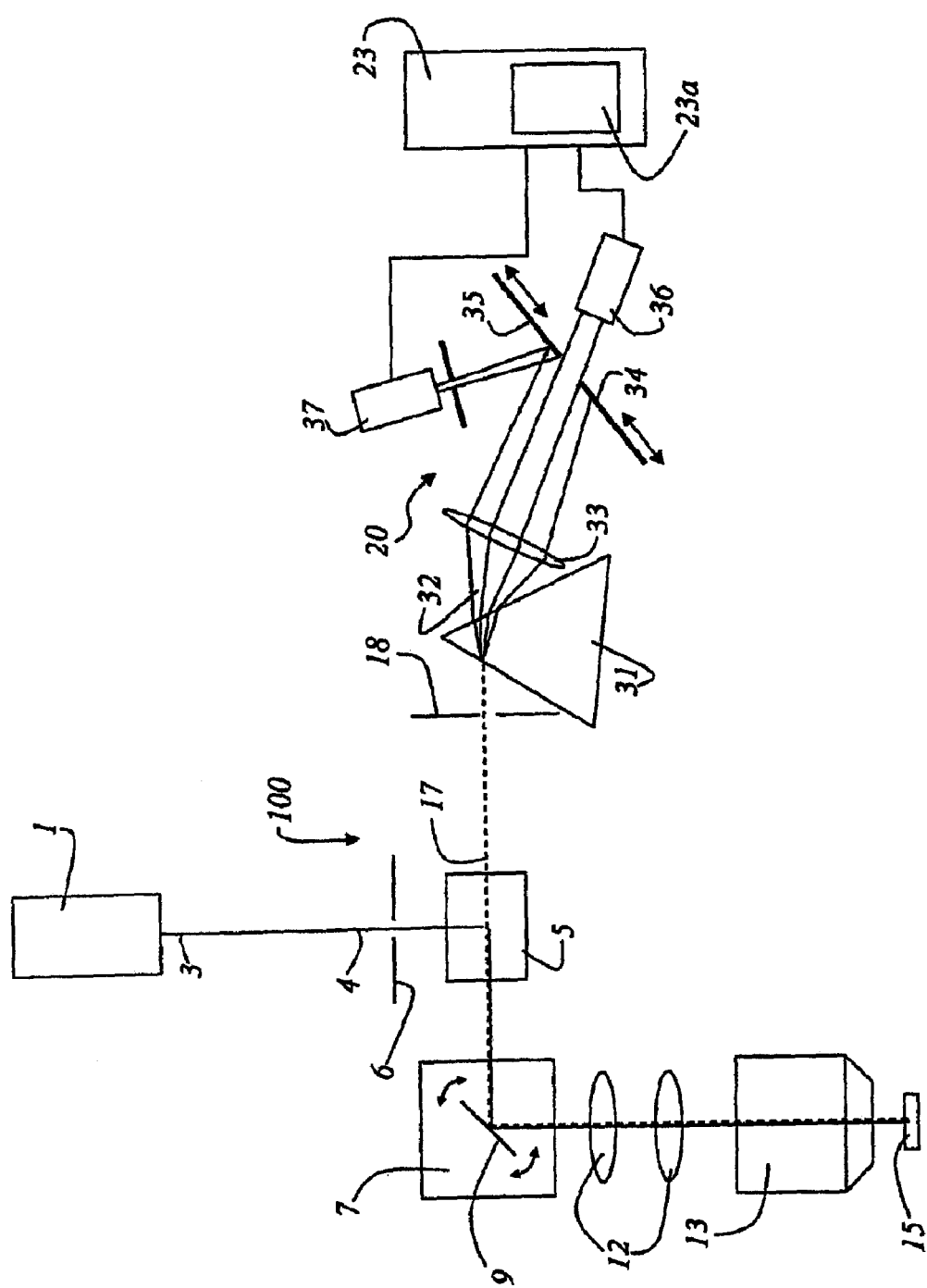
FIG. 1 schematically depicts a scanning microscope, the detector being preceded by an SP module.

FIG. 1 schematically shows the exemplary embodiment of a confocal scanning microscope 100. This is not, however, to be construed as a limitation of the invention, and one skilled in the art is well aware that the same invention-relevant components can also be installed in fluorometers, cytometers, and microscope systems of different design. Illuminating light 3 coming from at least one illumination system 1 is directed by a beam splitter or a suitable deflection means 5 to a scanning module 7. Before illuminating light 3 encounters deflection means 5, it passes through an illumination pinhole 6. Scanning module 7 encompasses a gimbal-mounted scanning mirror 9 that guides illuminating light 3 through a scanning optical system 12 and a microscope optical system 13 and over or through a specimen 15. In the case of non-transparent specimens 15, illuminating light 3 is guided over the specimen surface. With biological specimens 15 (preparations) or transparent specimens, illuminating light 3 can also be guided through specimen 15. For that purpose, non-luminous preparations are optionally prepared with one or more suitable dyes (not shown, since this is established existing art). The dyes present in specimen 15 are excited by illuminating light 3 characterized by its excitation spectra and emit light in a characteristic region of the spectrum peculiar to them. The spectra of the various dyes are superimposed, and the task is then to set scanning microscope 100 so as to make possible a separation, and thus detection, of the individual dyes present in specimen 15.

The light proceeding from specimen 15 is a detected light 17. It travels through microscope optical system 13 and scanning optical system 12 and via scanning module 7 to deflection means 5, traverses the latter, and arrives via a detection pinhole 18 at least one detector 36, 37 which is embodied as a photomultiplier. It is clear to one skilled in the art that other detection components, for example diodes, diode arrays, photomultiplier arrays, CCD chips, or CMOS image sensors, can also be used. Detected light 17 proceeding from or defined by specimen 15 is depicted in FIG. 1 as a dashed line. In detectors 36, 37, electrical detected signals proportional to the power level of the light proceeding from specimen 15 are generated. Because, as already mentioned above, light having a characteristic spectrum is emitted from specimen 15, it is useful to provide an SP module 20 in front of the at least one detector 36, 37. The data generated by the at least one detector 36, 37 are conveyed to a computer system 23. At least one peripheral device is associated with computer system 23. The peripheral device can be, for example, a display on which the user receives instructions for setting scanning microscope 100 or can view the current setup as well as the image data in graphical form. Also associated with computer system 23 is an input means that comprises, for example, a keyboard, a setting apparatus for the components of the microscope system, and a mouse.

SP module 20 (FIG. 2) is embodied in such a way that it can acquire a complete lambda scan, i.e. all the amplitudes, as a function of wavelengths proceeding from specimen 15 are recorded. In other words, a complete wavelength range is acquired so that all the waves proceeding from a specimen are therefore sensed. The data are transferred to computer system 23 and can then be presented on display in a manner definable by the user. Detected light 17 is spatially spectrally divided using a prism 31. A further possibility for spectral division is the use of a reflection or transmission grating. Spectrally divided light fan 32 is focused with focusing optical system 33 and then strikes a mirror stop arrangement 34, 35. Mirror stop arrangement 34, 35, the means for spectral spatial division, focusing optical system 33, and detectors 36 and 37 are together referred to as the SP module (or multi-band detector) 20.

Figure 2:
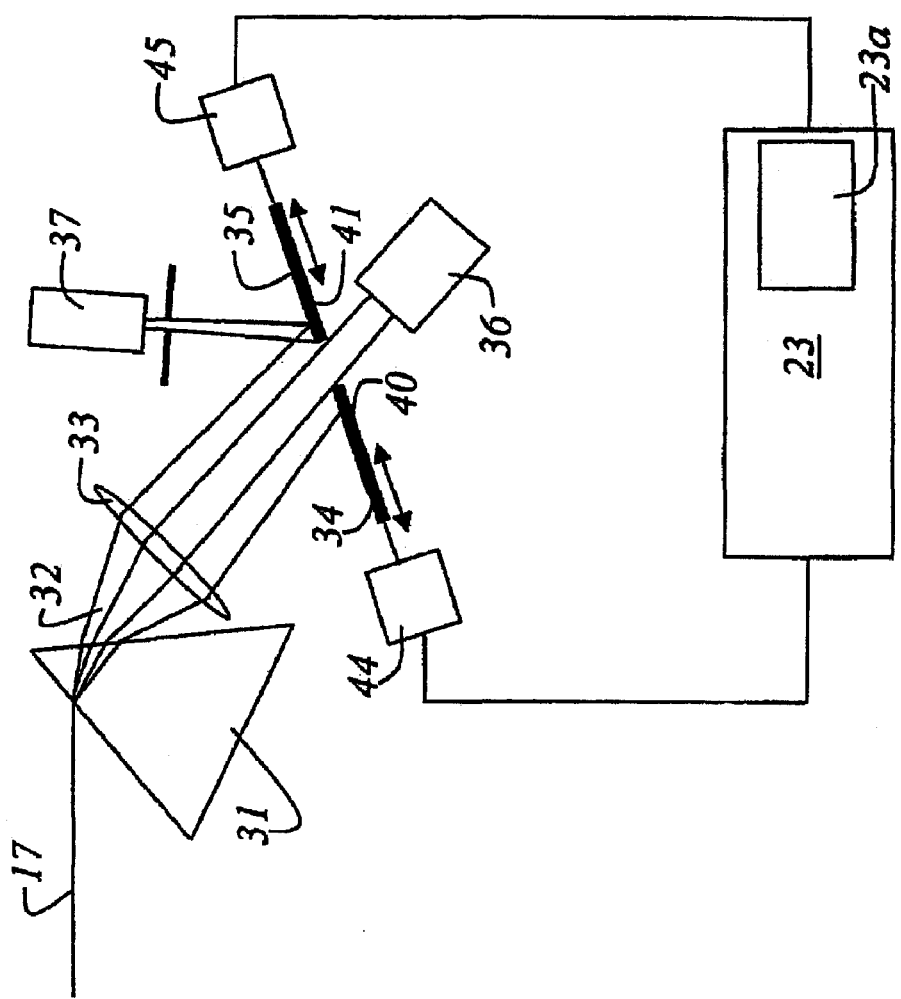
FIG. 2 schematically depicts the SP module in detail.

As is evident from FIG. 2, a desired portion of the spectrum of detected light 17 can be picked out or systematically selected by means of mirror stop arrangement 34, 35. In the exemplary embodiment depicted here, slit aperture arrangement 34, 35 is equipped with a first and a second slider 40 and 41 for selecting a single band portion of the spectrum. It is self-evident that for the selection of more than two spectral regions, a corresponding number of sliders must be provided. A corresponding increase in the mirror sliders results directly in an increase in the spectral bands acquired concurrently. A first motor 44 is associated with first slider 40, and a second motor 45 with second slider 41. Motors 44 and 45 permit a displacement of sliders 40 and 41 that is described in accordance with the method below. As a result of the displacement of sliders 40 and 41, only a portion of divided light fan 32 of detected light 17, containing only light of the preselected spectral region, passes through mirror stop arrangement 34, 35 and is detected by detector 36, which is embodied as a photomultiplier. Another portion of divided light fan 32 is reflected at mirror stop arrangement 35 and travels to detector 37, which is likewise embodied as a photomultiplier.

Figure 3:
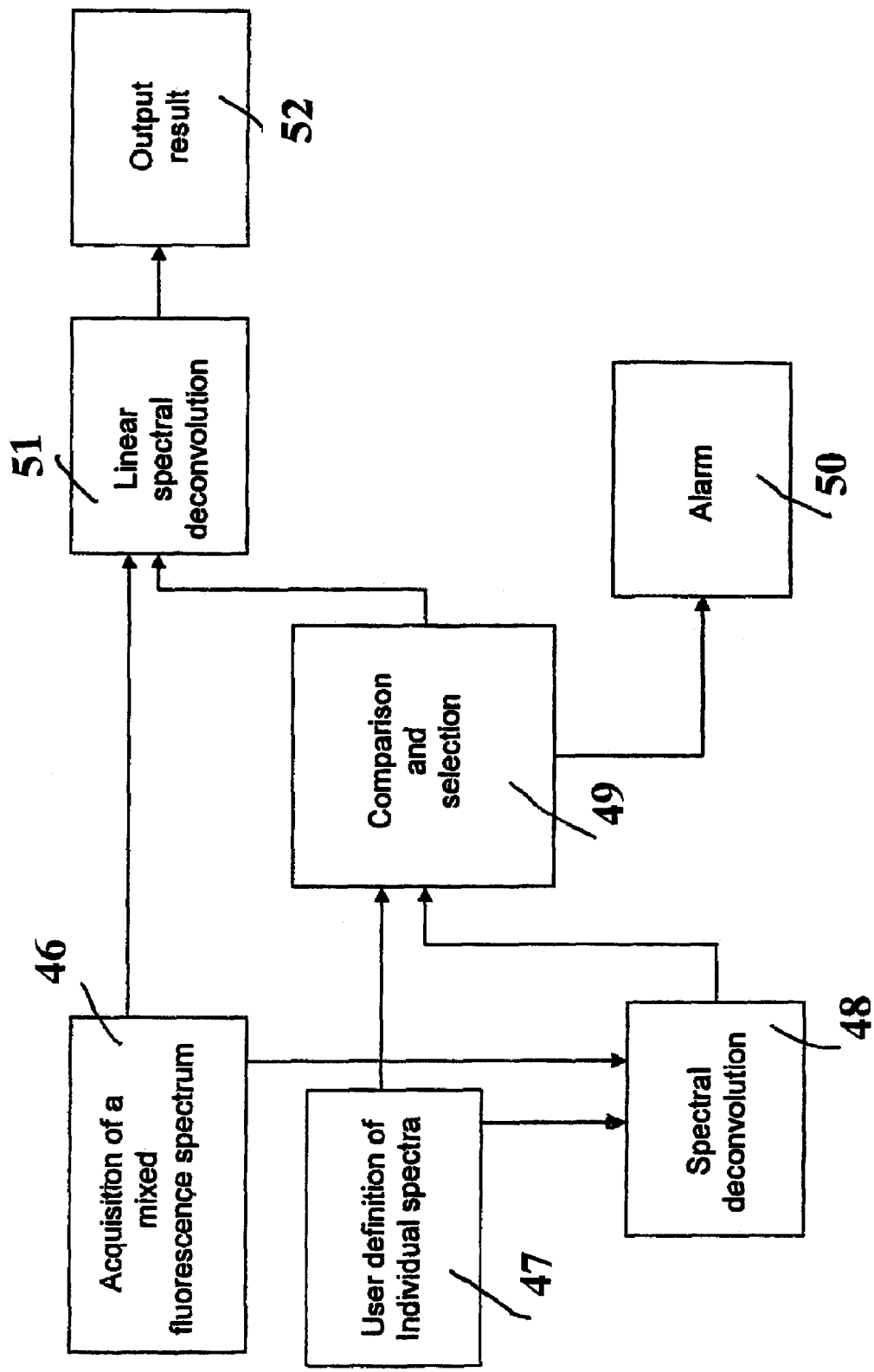
FIG. 3 schematically depicts execution of the method according to the present invention.

FIG. 3 discloses a schematic depiction of the execution of the method according to the present invention. A specimen 15 is, as a rule, equipped with more than one fluorescing dye. Each dye possesses an individual emission spectrum. It is easy to understand that the individual emission spectra of the individual dyes are superimposed, and thus form a mixed fluorescence spectrum. To determine which emission comes from which dye, a separation of the fluorescence spectra of the individual dyes present in specimen 15 is necessary. This is done by firstly (see 46, FIG. 3) acquiring a spectral scan, thereby ascertaining the mixed fluorescence spectrum of all the dyes present in specimen 15. The mixed fluorescence spectrum is acquired using SP module 20. A user also informs a computer system, associated with scanning microscope 100, of the dyes present in specimen 15 (see 47, FIG. 3). For each pixel a spectral intensity vector $I^{Det}$ is detected in the spectral scan during detection, that is made up of a linear combination of the emission spectra $s_i^{em}$ of the dyes introduced into the specimen. The emission spectra $s_i^{em}$ of the fluorescent dyes introduced into the specimen are combined into a mixed detection matrix $M_{Det}$. The fluorescence spectra associated with the respective dyes are stored in a database 23a (FIGS. 1,2) of the computer system 23. The database can, of course, be supplemented with the user's reference measurements. The acquired mixed fluorescence spectrum is spectrally deconvoluted (see 48, FIG. 3). The acquired and spectrally deconvoluted fluorescence spectrum, i.e. the individual spectra, are compared with the fluorescence spectra associated with the respective dyes from the database (see 49, FIG. 3). The result of the comparison determines how the method according to the present invention proceeds further. If the comparison is unsatisfactory, an alarm signal is generated (see 50, FIG. 3). The alarm signal 50 can be, for example, acoustic or optical in nature. A combination of both signal types is likewise conceivable. If the result of the comparison is acceptable, then lastly a linear deconvolution of the acquired mixed fluorescence spectrum (see 51, FIG. 3), and presentation on the associated display, are performed (see 52, FIG. 3).

The essential idea is the safeguard function. A variety of methods are possible for implementing it, one of which is outlined briefly below. Each pixel of a spectral image can be represented as a vector I. In that space, each individual dye constitutes a reference vector $I_{dye}^{REF}$ that identifies it. Observations of dye concentrations of that dye always lie on a straight line, through the origin, that is spanned by that reference vector. If there are two dyes, then all the observations lie in a plane spanned by both dye reference vectors. Three dyes result in a volume, four a hypervolume, etc. Each individual measurement point I can thus be broken down into two vectors $I=I_r+I_n$, where $I_r$ is the component in the relevant spanned manifold and $I_n$ the component perpendicular thereto. This breakdown can be performed using Hessian normal formalism, and is part of the tool kit of any graduate. The component $I_n$ corresponds to the component that does not correspond to the model. It is determined substantially by noise, and should be correspondingly small. The total energy (square of the absolute value) of this deviation should be correspondingly small in relation to the total energy within the model component; this is trivially easy to implement by way of a threshold value test.

The invention has been described with reference to a particular embodiment. It is self-evident, however, that changes and modifications can be made without thereby leaving the range of protection of the claims below.

What is claimed is:

1. In a scanning microscope a method for separating fluorescence spectra of dyes present in a specimen, comprising the steps of:
    acquiring a spectral scan of the specimen and thereby ascertaining an acquired mixed fluorescence spectrum of all the dyes present in the specimen;
    storing individual fluorescence spectra corresponding to the respective dyes present in the specimen in a computer system associated with the scanning microscope;
    spectrally deconvoluting the acquired mixed fluorescence spectrum to obtain spectrally deconvoluted measured individual spectra and comparing the measured individual spectra to the individual fluorescence spectra corresponding to the respective dyes;
    generating an alarm signal if comparing the measured individual spectra to the individual fluorescence spectra is unsatisfactory with regard to a safeguard function based on a threshold value;
    linearly deconvoluting the acquired mixed fluorescence spectrum if no alarm is generated and presenting a result of the deconvoluting steps on a display.

2. The method as defined in claim 1, wherein an excitation and emission spectra belonging to the individual dyes are stored in the database of the computer system.

3. The method as defined in claim 1, wherein the spectral scan of the detected light is performed by means of a spectral photometer SP module.

4. The method as defined in claim 3, wherein the individual spectra associated with the respective dyes are measured in the detected light by means of the SP module in such a way that by means of a mirror stop arrangement of the SP module, a desired portion of the spectrum of the detected light associated with the individual spectra is selected and detected.

5. The method as defined in claim 1, wherein in the spectral scan during detection, for each pixel a spectral intensity vector $I^{Det}$ is detected that is made up of a linearcombination of the emission spectra $s_i^{em}$ of the dyes introduced into the specimen.

6. The method as defined in claim 5, wherein the emission spectra $s_i^{em}$ of the fluorescent dyes introduced into the specimen are combined into a mixed detection matrix $M_{Det}$.

* * * * *